(12) United States Patent
Brady (10) Patent No.: US 11,768,189 B2
(45) Date of Patent: Sep. 26, 2023

(54) DETECTION, CHARACTERIZATION, AND MAPPING OF SUBSURFACE PFAS-STABILIZED VISCOELASTIC NON-NEWTONIAN LNAPLS USING RHEOLOGICAL METHODS

(71) Applicant: Patrick Richard Brady, Sisters, OR (US)

(72) Inventor: Patrick Richard Brady, Sisters, OR (US)

( * ) Notice: Subject to any disclaimer, the term of this patent is extended or adjusted under 35 U.S.C. 154(b) by 44 days.

(21) Appl. No.: 17/651,299

(22) Filed: Feb. 16, 2022

(65) Prior Publication Data

US 2023/0258619 A1     Aug. 17, 2023

(51) Int. Cl.
*G01N 33/24* (2006.01)
*G01N 13/02* (2006.01)
*G01N 27/04* (2006.01)

(52) U.S. Cl.
CPC .............. *G01N 33/24* (2013.01); *G01N 13/02* (2013.01); *G01N 27/04* (2013.01)

(58) Field of Classification Search
CPC ......... G01N 33/24; G01N 13/02; G01N 27/04
See application file for complete search history.

(56) References Cited

U.S. PATENT DOCUMENTS

| | | |
|---|---|---|
| 4,738,206 A | 4/1988 | Noland |
| 4,864,942 A | 9/1989 | Fochtman et al. |
| 4,977,839 A | 12/1990 | Fochtman et al. |
| 5,067,852 A | 11/1991 | Plunkett |
| 5,098,481 A | 3/1992 | Monlux |
| 5,213,445 A | 5/1993 | Ikenberry et al. |
| 5,228,804 A | 7/1993 | Balch |
| 5,230,167 A | 7/1993 | Lahoda et al. |
| 5,302,118 A | 4/1994 | Renegar et al. |
| 5,361,514 A | 11/1994 | Lahoda et al. |
| 5,424,045 A | 6/1995 | Orman et al. |
| 5,613,452 A | 3/1997 | Marchesi et al. |
| 5,622,864 A | 4/1997 | Buchanan |
| 5,836,718 A | 11/1998 | Price |
| RE36,222 E | 6/1999 | O'Ham |
| 6,000,430 A | 12/1999 | Nafz |
| 6,110,430 A | 8/2000 | Swisher, Jr. et al. |

(Continued)

FOREIGN PATENT DOCUMENTS

| | | | | |
|---|---|---|---|---|
| CA | 2912403 C | * | 7/2021 | ........... A01B 79/005 |
| EP | 0546649 A2 | | 6/1993 | |

(Continued)

*Primary Examiner* — Ryan D Walsh
(74) *Attorney, Agent, or Firm* — Raven Patents, LLC; Anton E. Skaugset (57) ABSTRACT

Methods of detecting, characterizing, and mapping an environmental subsurface PFAS-stabilized viscoelastic non-Newtonian light non-aqueous phase liquid (LNAPL), including collecting an environmental sample that is a fluid sample, or is collected as a solid that is subsequently extracted with water to generate a fluid sample; and where the environmental sample is associated with a location where it was collected; analyzing the fluid sample using one or more rheological methods; and correlating the rheological characteristics with a presence or an absence of the non-Newtonian LNAPL at the location where the environmental sample was collected.

16 Claims, 6 Drawing Sheets

(56) References Cited

U.S. PATENT DOCUMENTS

| | | | |
|---|---|---|---|
| 6,146,596 | A | 11/2000 | Hill et al. |
| 6,296,815 | B1 | 10/2001 | Walker et al. |
| 6,829,844 | B2 | 12/2004 | Brady et al. |
| 7,618,215 | B2 | 11/2009 | Haemers et al. |
| 8,348,551 | B2 | 1/2013 | Baker et al. |
| 9,636,723 | B2 | 5/2017 | Brady |
| 9,816,909 | B2 | 11/2017 | Friedrich et al. |
| 10,875,062 | B2 | 12/2020 | Brady |
| 11,484,922 | B2 * | 11/2022 | Brady ............... B09C 1/06 |
| 2001/0023852 | A1 | 9/2001 | Kato et al. |
| 2004/0240942 | A1 | 12/2004 | Richter |
| 2010/0018294 | A1 * | 1/2010 | Tonmukayakul ...... G01N 11/14 73/54.39 |
| 2010/0068821 | A1 * | 3/2010 | St. Germain ...... G01N 33/1826 436/140 |
| 2010/0263751 | A1 | 10/2010 | Ringuette |
| 2012/0152548 | A1 * | 6/2012 | Hinkel ............... G01N 24/081 166/305.1 |
| 2013/0087329 | A1 * | 4/2013 | Hewitt ................. E21B 43/26 166/250.12 |
| 2016/0303625 | A1 | 10/2016 | Desmarais et al. |
| 2019/0382652 | A1 * | 12/2019 | Brierley ................. C09K 8/03 |
| 2020/0179997 | A1 | 6/2020 | Ross et al. |
| 2020/0206793 | A1 | 7/2020 | Brady |
| 2022/0307961 | A1 * | 9/2022 | Brady ................ G01N 13/02 |

FOREIGN PATENT DOCUMENTS

| | | |
|---|---|---|
| EP | 2899528 A1 | 7/2015 |
| WO | WO-2022243809 A1 * | 11/2022 |

* cited by examiner

DETECTION, CHARACTERIZATION, AND MAPPING OF SUBSURFACE PFAS-STABILIZED VISCOELASTIC NON-NEWTONIAN LNAPLS USING RHEOLOGICAL METHODS

TECHNICAL FIELD

The present disclosure relates to methods for the detection, characterization, and mapping of contaminants in subsurface soils and fluids. More particularly, the present disclosure relates to the detection, characterization, and mapping of subsurface PFAS-stabilized colloidal viscoelastic non-Newtonian light non-aqueous phase liquids (LNAPLs). These non-Newtonian LNAPLs function as subsurface source structures that generate PFAS groundwater plumes.

BACKGROUND

Per- and polyfluoroalkyl substances (PFAS, or perfluorinated alkylated substances) include thousands of different synthetic organofluorine compounds that feature multiple fluorine atoms attached to an alkyl chain. PFASs typically include alkyl chains that are at least partially fluorinated, and may include one or more perfluoroalkyl moieties, alkyl chains in which every hydrogen atom has been replaced by fluorine.

PFAS, and in particular perfluorinated surfactants, exhibit highly useful physical properties and so are commonly used in a wide variety of industries and incorporated into a multitude of consumer products. As a result, PFAS has been migrating into the environment for decades. In just one example, the aqueous film forming foams (AFFFs) used by firefighters to extinguish liquid hydrocarbon fires rely on PFAS to stabilize the foams and render them effective. Unfortunately, AFFFs are typically discharged directly into the environment both during training exercises and when used to extinguish actual fires.

When PFAS enters the environment, it generally migrates into groundwater. Due to their unique physical properties, PFAS and related compounds do not degrade in the environment, and in addition cause groundwater to flow faster. As a result, environmental PFAS forms subsurface plumes that are typically dilute, widespread and can extend for miles. Because PFAS are used in so many applications, there may be numerous sources of groundwater contamination in relatively close proximity, particularly in urban areas. As a result, in addition to being extremely large and dilute, PFAS groundwater plumes are typically the result of the comingling of plumes from several different sources of PFAS contamination.

The United States Environmental Protection Agency (EPA) has established a health advisory that sets an upper limit for PFAS of 70 parts per trillion for drinking water, which is an extremely low standard compared to other regulated chemical compounds. Unfortunately, more recent PFAS toxicology studies have indicated that an even lower concentration would be more appropriate. PFAS has already been declared a hazardous waste in some states and is expected to be listed as a federal hazardous waste in the not-too-distant future. The detection and remediation of PFAS plumes will soon become a high priority. The high cost of such remediation will unfortunately guarantee long-term litigation related to the identification of responsibility for such plumes.

Unfortunately, the inability of traditional investigative methods to detect subsurface PFAS plume source structures (non-Newtonian LNAPLs), coupled with the extremely low standard for PFAS in groundwater, mean that such sources are largely unidentified.

What is needed are more sensitive methods of detecting invisible PFAS viscoelastic non-Newtonian LNAPLs in order to facilitate remediation projects in PFAS-contaminated areas, making them more discerning and efficient. At the same time, a method of resolving entangled commingled PFAS groundwater plumes in order to identify their origins would help to accurately assign responsibility for such contamination, also facilitating a more timely cleanup.

SUMMARY

The present disclosure is directed to methods for the detection, characterization, and mapping of environmental viscoelastic non-Newtonian light non-aqueous phase liquids.

In an example, the disclosure is directed to a method of detecting an environmental viscoelastic non-Newtonian light non-aqueous phase liquid (LNAPL), including collecting an environmental sample, wherein the environmental sample is either collected as a fluid sample, or is collected as a solid that is subsequently extracted with water to generate the fluid sample; and where the environmental sample is associated with a location where it was collected; analyzing the fluid sample using one or more rheological methods; and correlating the rheological characteristics with a presence or an absence of the non-Newtonian LNAPL at the location where the environmental sample was collected.

In another example, the disclosure is directed to a method of identifying a source formulation for an environmental viscoelastic non-Newtonian light non-aqueous phase liquid (LNAPL), including collecting an environmental sample, where the environmental sample is either collected as a fluid sample, or is collected as a solid that is subsequently extracted with water to generate the fluid sample; characterizing the fluid sample using one or more rheological methods; and correlating the rheological characteristics with the source formulation for the non-Newtonian LNAPL.

In another example, the disclosure is directed to a method of deconvoluting an environmental contamination, including collecting a plurality of environmental samples that include a mixture of man-made viscoelastic fluid and natural soil colloids, wherein each environmental sample is either collected as a fluid sample, or is collected as a solid that is subsequently extracted with water to generate the fluid sample; characterizing one or more rheological properties of the plurality of fluid samples; correlating the characterized rheological properties of the plurality of fluid samples with one or more source formulations of the man-made viscoelastic fluid; characterizing one or more colloidal properties of the plurality of fluid samples with a presence of one or more natural soil colloids in the fluid samples; correlating the one or more natural soil colloids in the fluid samples with a three-dimensional path through the environment for each of the source formulations of the man-made viscoelastic fluids; and identifying an origin point for each of the man-made viscoelastic fluids by combining the correlated source formulations of one or more of the man-made viscoelastic fluids with the three-dimensional path through the environment for the corresponding man-made viscoelastic fluid.

DETAILED DESCRIPTION

In order to appreciate the methods of the present disclosure, it is necessary to understand the kinds of PFAS formulations that reach the environment, and how they then interact with soil and groundwater.

PFAS are typically released into the environment as part of a man-made colloidal formulation such as AFFF, in which PFAS functions as a surfactant to stabilize the formulation. Colloidal solutions or systems are defined as mixtures in which microscopically small amounts of one substance are suspended in another substance. In a true colloid, the dispersed substance remains suspended, and does not dissolve or settle out of the material in which it is suspended. The colloid may be formed from particles, droplets, bubbles, also thin films on large surfaces, and liquid films The dispersed substance in a colloid (whether particles, droplets, or bubbles) has at least one dimension between about 1 to 1000 nanometers ($10^{-9}$ meters).

From a particulate size standpoint, colloidal chemistry occupies a space between classic chemistry and classic Newtonian physics; colloidal chemistry is the "in between" science. Colloidal droplets are extremely small and may exhibit a quantum size effect, which may make classic Newtonian physics inappropriate, and require selected aspects of quantum mechanics in order to properly describe the behavior of colloidal particles. In addition, colloids have a high surface area to mass ratio, providing unique properties and utilities. Colloidal particles are also in constant Brownian motion within their host medium.

Currently the environmental remediation industry and regulatory agencies employ expertise arising from either classic chemistry (i.e., chemists and toxicologists) or classic Newtonian physics (i.e. geologists, hydrogeologists and engineers). Chemists will tend to view PFAS as a chemical in solution, while geologists and engineers tend to view PFAS as a solute transport mechanism. While both views can be important elements of remediation, a third perspective is required in order to fully understand the behavior of PFAS in the environment, that of rheology, or the study of flow and deformation of viscoelastic fluids.

Newtonian fluids can be characterized by a single coefficient of viscosity for a specific temperature. Although their viscosity will change with temperature, the viscosity of Newtonian fluids does not change with the strain rate. The class of fluids whose viscosity changes with the strain rate (the relative flow velocity) are called non-Newtonian fluids. Rheology accounts for the behavior of these non-Newtonian fluids, by characterizing the reaction of such fluids to rate of change of strain or strain rates. For example, some non-Newtonian fluids may exhibit pseudoplasticity, where an increase in relative flow velocity will cause a reduction in viscosity, for example, by stirring. Other non-Newtonian materials may exhibit show the opposite behavior, rheopecty, where viscosity increases with relative deformation AFFF in particular is a PFAS-stabilized microemulsion concentrate that is injected into a water stream to create firefighting foam. The AFFF concentrate itself is a non-Newtonian fluid with pseudoplastic and thixotropic properties. These properties are what gives the AFFF foams their advantageous properties, but also explain their subsequent subsurface migratory path in the environment, their mixing with natural soil colloidal complexes, and the dynamic nature of their location.

Figure 1:
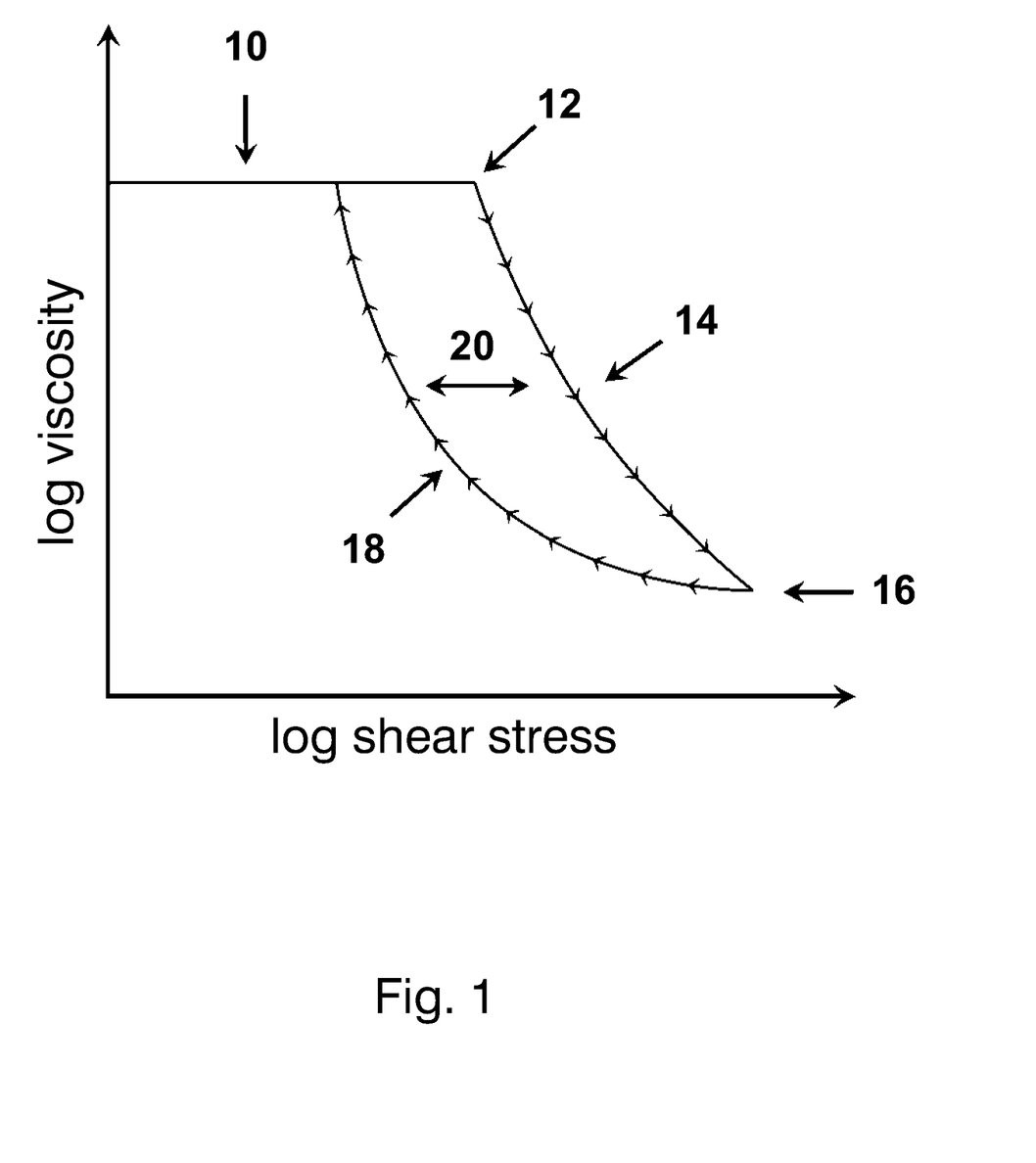
FIG. 1 is a plot of log viscosity vs. log shear stress for a non-Newtonian fluid.

Viscosity is a given fluid's resistance to flow and deformation, while shear stress is the velocity gradient perpendicular to a shear plane. FIG. 1 is a representative power law graph (log viscosity vs. log shear stress) for AFFF formulations, showing how viscosity changes with changes in applied shear stress. Because the AFFF formulation is a non-Newtonian fluid, the relationship between viscosity and shear stress exhibits a non-Newtonian Loop defining that fluid's operational window, subsurface migration path, natural soil colloidal complex mixing behavior and dynamic location.

As shown, the viscosity values for the formulations are constant under lower shear stress values, which result in a flat line called the Newtonian plateau at 10. Under low shear stress, the formulation behaves like a Newtonian fluid with a consistent viscosity value in response to changes in shear stress. However, when the applied shear stress increases to a certain value the viscosity of the formulation will begin to decrease. This point is reached when the powers law index drops below 1, which is referred to as the activation shear, at 12. Beyond the activation shear, formulation viscosity rapidly decreases with increasing shear stress. This rapid viscosity decline is referred to as the power law region, at 14. within the powers law region, a powers law index can be calculated from the slope of the plot that is unique to each non-Newtonian fluid. The powers law region 14 reflects a functional relationship between two quantities, where a relative change in one quantity results in a proportional relative change in the other quantity, and is characteristic of, and a reflection of, the non-Newtonian character and the pseudoplasticity of AFFF formulations. The slope within the powers law region 14 identifies the formulation as a shear thinning viscoelastic fluid (non-Newtonian microemulsion).

AFFF formulations have a design point, at 16, where formulation viscosity meets a design specification. The particular viscosity at design point 16 depends on the desired function of the colloidal formulation. In the case of AFFF formulations, formulation viscosity is reduced to a point where a foam can be produced when the AFFF formulation is injected into a firehose nozzle. The water stream from the nozzle produces a velocity gradient perpendicular to the formulation injection point, which causes the viscosity to change according to the power law region. The AFFF formulation creates a film structure, which then forms bubbles through self-assembly on either side of the water film creating bubbles and foam. AFFF foams are typically 3% to 6% AFFF formulation by volume after mixing with water and applied using a firehose nozzle, and can be considered to be mostly water held together by a thin lower viscosity film of the AFFF formulation.

As shown in FIG. 1, formulation viscosity remains near the design point 16 for a limited time once shear stress is reduced or removed altogether. Design point viscosity gradually returns to the original formulation viscosity in the Newtonian plateau 10. The increasing viscosity slope is the formulation's thixotropic region, at 18. The difference between the power law region 14 and the thixotropic region 18 is known as the degree of hysteresis, at 20, and defines a given formulation's operational window of utility. It is the behavior reflected by the degree of hysteresis and the thixotropic region that will define a spilled formulation's subsurface migration path and migration timeframe.

Figure 2:
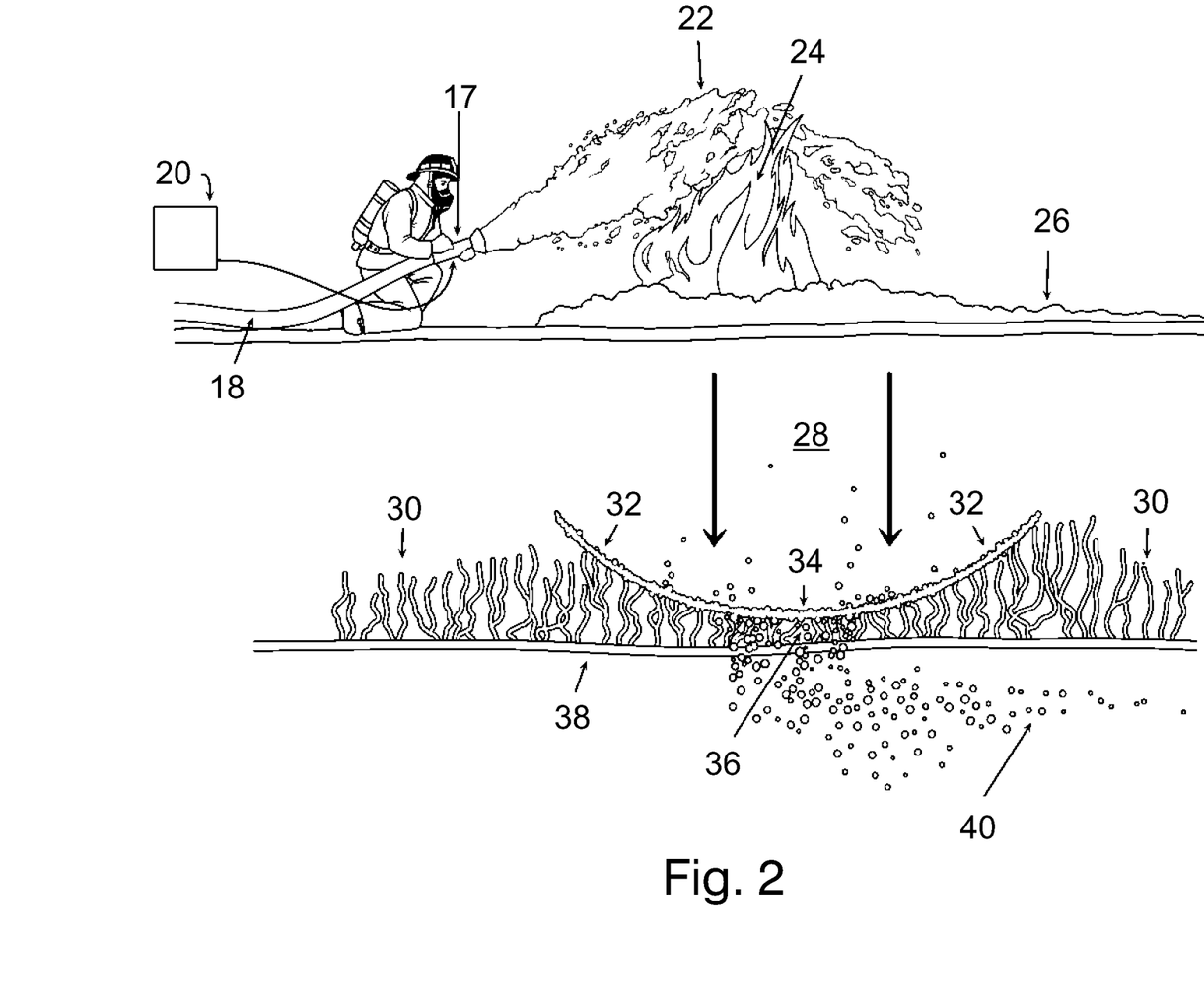
FIG. 2 is a diagram showing the use of AFFF firefighting foam, and its entry into the environment.

FIG. 2 depicts a typical AFFF foam firefighting arrangement. A fire nozzle 17 combines a large volume stream of high velocity/high pressure water 18 with AFFF formulation concentrate 20 at the design specifications, which cause multiple phenomena to occur almost instantaneously. The activation shear point 12 of the AFF formulation is reached when the formulation contacts the water stream. The formulation then immediately enters the power law region 14 where viscosity is substantially reduced to the design point 16. Foam 22 is immediately formed at the exit of the firehose nozzle 17, which is then broadcast over a liquid hydrocarbon fire 24 to extinguish the fire.

After discharge the AFFF foam eventually decays over time (i.e., the bubbles of the foam collapse), generating a wastewater/formulation mixture 26 that then migrates into the subsoil 28, where it mixes with naturally-occurring soil colloidal complexes. Naturally-occurring soil colloids are the most active constituent of a given soil system and they often determine the physical and chemical properties of a particular soil. The PFAS-containing colloids present in AFFF wastewater mix with naturally-occurring soil colloids, and the low surface tension and thixotropic properties of the AFFF-based colloid mixture facilitates entrainment and subsequent transport of natural soil colloidal complexes with the wastewater/formulation mixture 26.

Eventually, the resulting mixture encounters the top of the capillary fringe 30. The mixture increases its viscosity over time due to its thixotropic nature, which further enhances natural soil colloidal complex mixing, and reconstitutes back to its original viscosity within the Newtonian plateau 10. Due to the decreased surface tension of the wastewater mixture, the capillary fringe is depressed, forming a localized depression 32 where a non-Newtonian LNAPL 34 will accumulate as a thin film.

These non-Newtonian LNAPLs follow seasonal water table fluctuations at the saturation surface boundary at the top of the capillary fringe, and act as reliable long-term PFAS groundwater source structures able to deliver PFAS and other compounds across the residual capillary fringe 36 to the water table (groundwater) 38, and thereby producing large dilute plumes of PFAS and other compounds 40, which can travel for miles.

Studies have shown that AFFF in wastewater is well above its critical micelle concentration (CMC). The CMC is the concentration where a surfactant saturates a surface of a liquid and begins to form micelles and other complex structures in the bulk of the liquid. Concentrations above the CMC support formation of a microemulsion, or colloidal solution.

The existing environmental remediation industry and regulatory agencies are highly focused on a chemical-specific approach when investigating and remediating environmental contamination. The only exception to this chemical-specific approach in the existing regulatory framework is related to LNAPLs, and there is a defined pathway for closure of sites due to the presence of an LNAPL. Unfortunately, classic LNAPLs are related to contamination with petroleum formulations such as gasoline and diesel fuel, which can include any of hundreds of specific hydrocarbon "C" ranges and additives. Petroleum LNAPLs are non-polar Newtonian fluids, and thus will behave in a more conventional way from the perspective of both chemists and engineers.

Non-Newtonian LNAPLs however, such as those that arise from AFFF discharge, do not behave in such a conventional manner, and the lack of expertise in non-Newtonian colloids and rheology (the study of flow and deformation of viscoelastic fluids) in regulatory agencies and the environmental remediation industry result in a blind spot regarding the behavior of non-Newtonian LNAPLs. These complex viscoelastic fluids require a different investigative paradigm in order to be effectively detected and characterized, one that employs rheological methods.

The present disclosure is directed to the use of rheological methods, or the study of flow and deformation of complex viscoelastic fluids to detect, characterize, and map the presence of environmental non-Newtonian LNAPLs and their related groundwater plumes. These PFAS-stabilized colloids, mixed with natural soil colloids, form a unique composition that can be fingerprinted to a specific spill source formulation and to a specific location.

Sample Collection

The present methods can be used to identify the presence and/or to characterize a non-Newtonian LNAPL in the environment through the testing of an environmental sample obtained at a location of interest. More typically, a multitude of environmental samples can be collected, and provided that the location where each sample is collected is associated with that sample the location data permits the detection and analysis of size and location of a groundwater plume, or of a non-Newtonian LNAPL that is acting as a groundwater plume source, and/or facilitate the backwards tracing of the movement of a PFAS-containing contaminant through the environment.

Although the rheological methods of the present disclosure are typically performed on a fluid sample, the environmental sample collected for the present methods may be a fluid sample, a semi-solid sample, or a solid sample, without limitation.

As used herein, an environmental sample is a sample collected in situ at a location of interest. A fluid sample is or is derived from an environmental sample. Where the environmental sample is or includes a fluid, the fluid is typically but not exclusively an aqueous fluid. The fluid sample can be analyzed directly, or can be subject to one or more purification steps, such as for example filtration, prior to analysis.

The environmental sample may be or may include a fluid that is groundwater, pore water, perched water, excavation water, surface water, or leachate, among others. The environmental sample may be collected, for example, from a surface body of water, from a well, from a borehole, and/or from the leachate from a waste facility. Where the sample is collected from a well, the well may be a monitoring well, a water supply well, or any other type of well. Where the sample is collected from a borehole, the borehole may be formed by direct-push drilling, or any other suitable drilling method.

Where the environmental sample is or includes a solid, the solid may be or include a soil sample, a porous media sample, or a colloidal media sample, among others. The solid environmental sample may be collected from any suitable environmental source, including but not limited to soil borings, boreholes (including direct-push drill boreholes), surface soil, or any suitable excavation.

Where the environmental sample is or includes a solid, the sample is combined with an appropriate fluid, such as for example water, methanol, ethanol, or other relatively polar solvent, and the fluid is then analyzed directly as a fluid sample, or can be subjected to one or more purification steps prior to analysis as a fluid sample. Where the sample is being combined with an appropriate fluid, it can be immersed in the fluid, shaken with the fluid, dissolved in the fluid, or placed in contact with the fluid using any other appropriate method. Typically, the sample is combined with a fluid that is distilled water.

As used herein, fluid sample can refer to a fluid sample collected in situ at an environmental location, a liquid obtained from a solid or semi-solid sample collected in situ at an environmental location (such as by immersion or extraction), or a sample taken at the surface of such a fluid sample, where non-Newtonian LNAPLs may be concentrated.

Rheological Analysis Techniques

The fluid samples of interest may be analyzed using any suitable analytical methodology. Typically, the fluid samples will be analyzed using one or more rheological techniques to determine one or more of the following characteristics: I. Surface energy footprint, II. Residual functionality, and III. Colloidal characteristics.

Surface Energy Footprint

The surface energy characteristics of a fluid sample may be readily determined using known methods and instruments. In particular, a surface energy footprint for a fluid sample can be determined by measuring the surface tension of the fluid sample, measuring the dynamic surface energy of an immersion substrate after exposure to the fluid sample, and measuring the electrical conductivity or resistivity of the fluid sample.

The energy of a surface can be measured directly. The most common way to measure surface energy is through the measurement of contact angles. A contact angle is the angle defined by a liquid—vapor interface where a drop of liquid meets a solid surface, and reflects the relative strength of the interactions between the liquid, the solid, and the vapor.

Where a liquid has a high degree of surface tension, such as water, and the surface is relatively nonpolar, measured contact angles can be very high. Alternatively, a drop of nonpolar liquid on a nonpolar surface will typically spread out, exhibiting a very low contact angle.

The measured surface energy of a substance is typically a product of two types of interactions with the surface: Polar interactions, and dispersive interactions. Polar interactions are due to Coulomb interactions between permanent dipoles and between permanent and induced dipoles (e.g. hydrogen bonds), while dispersive interactions are caused by temporary fluctuations of charge distribution in the atoms/molecules involved (i.e. van der Waals interaction). The surface energy of a surface can therefore be expressed by the formula:

$$\sigma_t = \sigma_p + \sigma_d$$

where $\sigma_t$ is the measured total surface energy of a surface as determined experimentally, $\sigma_p$ is the polar component of the surface energy, and $\sigma_d$ is the dispersive component of the surface energy. These components of total surface energy can be measured using any suitable methodology, but are typically calculated by measuring and/or evaluating contact angles determined for both polar and non-polar liquids on the surface under evaluation.

Amphiphilic compounds, such as surfactants, have a tendency to undergo self-assembly on high energy surfaces, due largely to Coulombic interactions, and can create ordered layers or films on the surface. The surface energy of a given surface will decrease or increase and exhibit altered characteristics (changes in relative polar and dispersive portions of total surface energy) after being covered by such self-assembled amphiphilic structures.

The analysis methods disclosed herein therefore involve measuring the surface energy of a clean substrate having relatively high surface energy by measurement of contact angles at that surface. The substrate can then be exposed to the fluid sample of interest. If amphiphilic compounds are present in the media, such as PFAS, then they should spontaneously adsorb onto the high energy surface of the substrate, changing the surface energy characteristics of the substrate surface. Contact angle measurement of the substrate surface before and after such exposure can then provide qualitative or quantitative information about the presence, amount, and even the type of PFAS-containing viscoelastic fluid from which the fluid sample was derived.

Surface energy footprint determination may include measuring one or more of a total surface tension, static surface tension, dynamic surface tension, a polar component of the total surface tension, a dispersive component of the total surface tension, and early surface age slope data. When determining the surface tension of a fluid sample, any appropriate methodology and/or surface tensiometer instrument may be used. Static surface tension may be determined using the Du Noüy ring method, for example, while dynamic surface tension may be determined using the bubble pressure method. More particularly, surface tension may be determined via contact angle measurement.

In particular, patent application Ser. No. 17/214,431, filed Mar. 26, 2021, describes methods, apparatus, and kits for detecting and optionally quantifying amphiphilic compounds in the environment using surface energy measurements of fluid samples. The disclosure of application Ser. No. 17/214,431 is hereby incorporated by reference, for any and all purposes.

As described by appl. Ser. No. 17/214,431, dynamic surface energy (DSE) of a substrate (i.e. an immersion tab) can be determined using contact angle measurement. Such a determination may include determining a base dynamic surface energy of the surface of the immersion tab before exposure to the fluid sample. The immersion tab is then immersed in the fluid sample of interest, and the change in dynamic surface energy is measured. The change in dynamic surface energy may include the total change in dynamic energy, the change in the polar component of the dynamic surface energy, and/or the change in the dispersive portion of the dynamic surface energy.

These values may be determined from, for example, measuring the change in contact angle of a liquid on the immersion tab, measuring the change in hydrophobicity of the surface of the immersion tab, and measuring the change in wetting envelope of the surface of the immersion tab.

Although any contact angle measuring device can be used for such determinations, it is preferable that the contact angle measurement apparatus be relatively small and lightweight, so that it can be readily used in the field. An exemplary contact angle measurement apparatus useful in the context of the present disclosure was described by Friedrich et al. in U.S. Pat. No. 9,816,909 (hereby incorporated by reference for all purposes).

Surface energy determination can include, or can be augmented by, information collected at the location where the corresponding environmental sample was collected. Such localized information may include one or more of a measured in situ soil moisture, a measured in situ soil cation exchange capacity (CEC), a measured elevation of the top of the capillary fringe, and a measured subsurface electrical conductivity and/or resistivity.

Where the elevation of the top of the capillary fringe is being measured, such measurement may be obtained using, for example, ground-penetrating radar or soil moisture profile analysis, among other methods.

Where subsurface electrical conductivity or resistivity is being measured, such measurement may be obtained using, for example, a ground surface survey, a ground electromagnetic survey, or down-hole borehole survey, among others.

The measurement of an electrical conductivity or resistivity of a fluid sample can be accomplished with any of a variety of appropriate conductivity meters and/or sensors, which are readily available.

Residual Functionality

An important aspect of detecting and/or characterizing the presence of non-Newtonian LNAPLs is the characterization of the foaming ability of a given fluid sample. The presence of PFAS in the sample will confer foamability on the resulting fluid. This residual foaming ability can be qualitatively or quantitatively determined.

The foaming properties of surfactants (amphiphiles) may characterized by determining one or more of foam height, bubble sizes and their statistical distribution within the foam, form formation behavior of heavily foaming liquids using stirring cycles, moisture and drainage behavior of foam using its electrical conductivity, foam decay via decrease in total foam height and foam volume over time, head retention value, maximum foam volume and liquid volume when foaming is at a maximum, liquid content and foam structure, and foam half life (time for reduction of liquid volume in foam and foam volume), among others.

Some or all of the foaming properties may be measured using a foam analyzer. Some foam analyzers function by comparing the relative stability of a foam by measuring the effect of an arbitrary standard destructive mechanism acting upon a volume of foam during production under standard conditions and protected from adventitious destructive forces. Any suitable foam analyzer may be used to determine residual foaming ability, including those commercially available from KRÜSS GmbH.

Colloidal Characteristics

Any of the properties typically associated with colloidal compositions may be measured in order to characterize the viscoelastic fluid present in a fluid sample, such as persistence of suspension, Brownian movement, and light-scattering, among others.

Where the fluid sample is subjected to light scattering analysis, the light scattering analysis may be used to determine colloidal particle size and size distribution, the polydispersity index, and/or the zeta potential (electrokinetic potential) of the colloid.

Alternatively, or in addition, the power law index of the fluid sample may be determined using a rheometer. As indicated above, the particular power law behavior of a given material can be characteristic of that material, permitting fingerprinting of a given AFFF formulation found in the environment.

Alternatively, or in addition, the fluid sample may be subjected to a large-amplitude ocellary shear (LAOS) analysis in order to characterize a non-linear functionality of a given fluid sample, helping to characterize the source of the sample.

Alternatively, or in addition, the fluid sample may be used to determine a dimensionless Weissenberg number for the viscoelastic fluid in the fluid sample.

Alternatively, or in addition, the fluid sample may be used to determine a dimensionless Deborah number for the viscoelastic fluid in the fluid sample.

Additionally, a Pipkin diagram showing flow regimes of the viscoelastic fluid in the fluid sample may be prepared related to the determined Weissenberg number and Deborah number, further characterizing the viscoelastic fluid in the fluid sample.

Mapping and Tracing via Overlay Analysis

After a plurality of fluid samples has been characterized, valuable information about the subsurface distribution of contaminants may be obtained by plotting the obtained data on one or more maps, associating such data with the location where the related fluid sample was obtained.

For example, one or more of the contributing aspects of the surface energy footprint data set, the residual functionality data set, and the colloidal characteristics data set can be plotted on a map, either singly, or in combination.

The presence and/or the migration path of a non-Newtonian LNAPL may be obtained by detecting significant deviations (anomalies) from background conditions. For example, the observation of a deviation from background conditions above the location of the capillary fringe may be used to determine the migration path of a non-Newtonian LNAPL, while the observation of a deviation from background conditions at the capillary fringe may be used to determine the dynamic location of a non-Newtonian LNAPL.

It should be appreciated that mapping the characteristic data sets may include two-dimensional and three-dimensional mapping techniques. In particular, three-dimensional mapping may be accomplished by sampling via soil borings, direct push drill borings, and direct excavations, or via macro-sampling and analysis.

Additionally, it should be appreciated that a statistical analysis of anomaly data sets may be used to determine a unique character for a given environmental contaminant, helping to identify a source for the contamination, and potentially establish responsibility for remediation costs.

Methods

Figure 3:
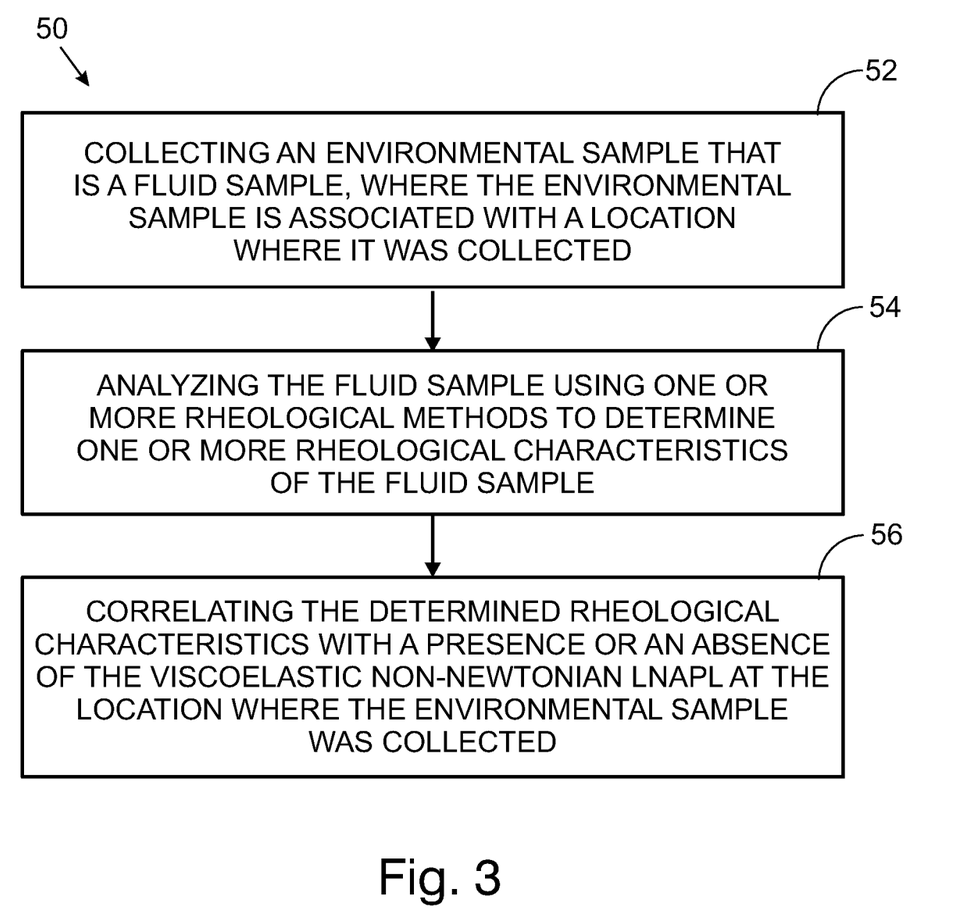
FIG. 3 is a flowchart of an illustrative method according to the present disclosure.

The analytical methods and strategies of the present disclosure lend themselves to an advantageous method of detecting an environmental non-Newtonian light non-aqueous phase liquid (LNAPL), as set out in flowchart 50 of FIG. 3, including collecting an environmental sample, where the environmental sample is associated with a location where it was collected; at step 52 of flowchart 50; analyzing the fluid sample using one or more rheological methods to determine one or more rheological characteristics of the fluid sample, at step 54 of flowchart 50; and correlating the rheological characteristics with a presence or an absence of the non-Newtonian LNAPL at the location where the environmental sample was collected, at step 56 of flowchart 50.

Figure 4:
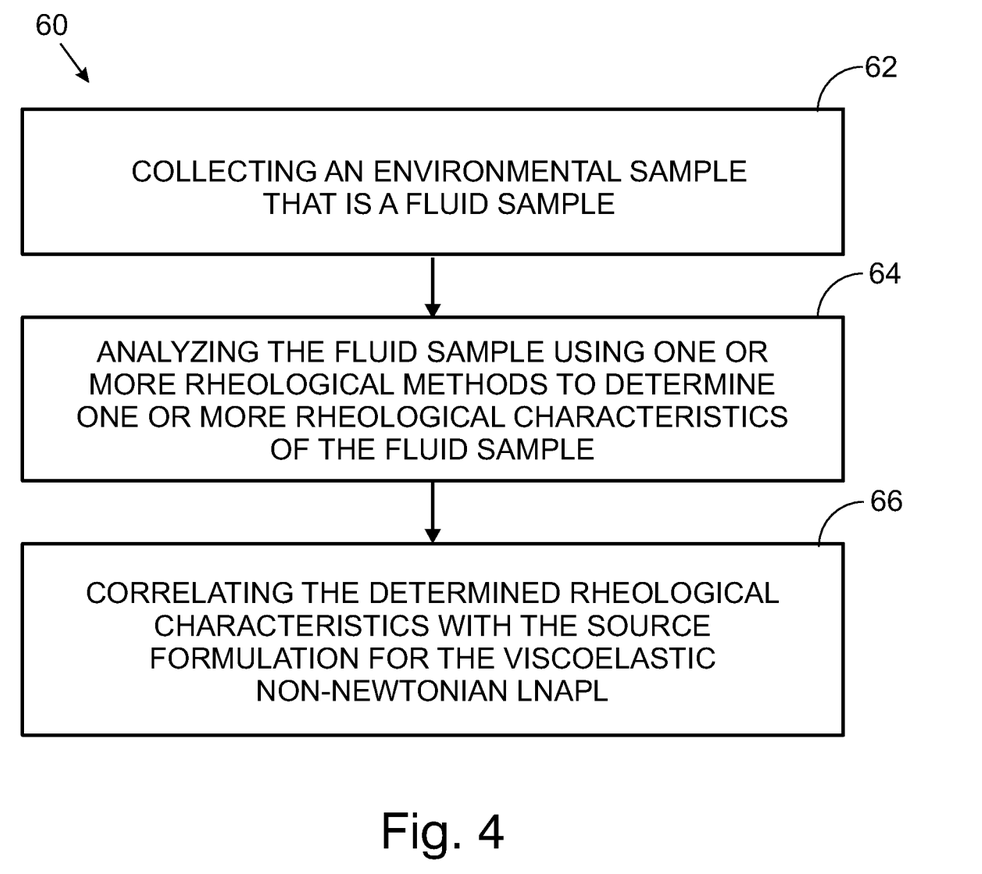
FIG. 4 is a flowchart of another illustrative method according to the present disclosure.

The analytical methods and strategies of the present disclosure additionally lend themselves to an advantageous method of identifying a source formulation for an environmental non-Newtonian light non-aqueous phase liquid (LNAPL), as set out in flowchart 60 of FIG. 4, including collecting an environmental sample that is a fluid sample, at step 62 of FIG. 4, characterizing the fluid sample using one or more rheological methods to determine one or more rheological characteristics of the fluid sample, at step 64 of FIG. 4; and correlating the determined rheological characteristics with the source formulation for the non-Newtonian LNAPL, at step 66 of FIG. 4.

Figure 5:
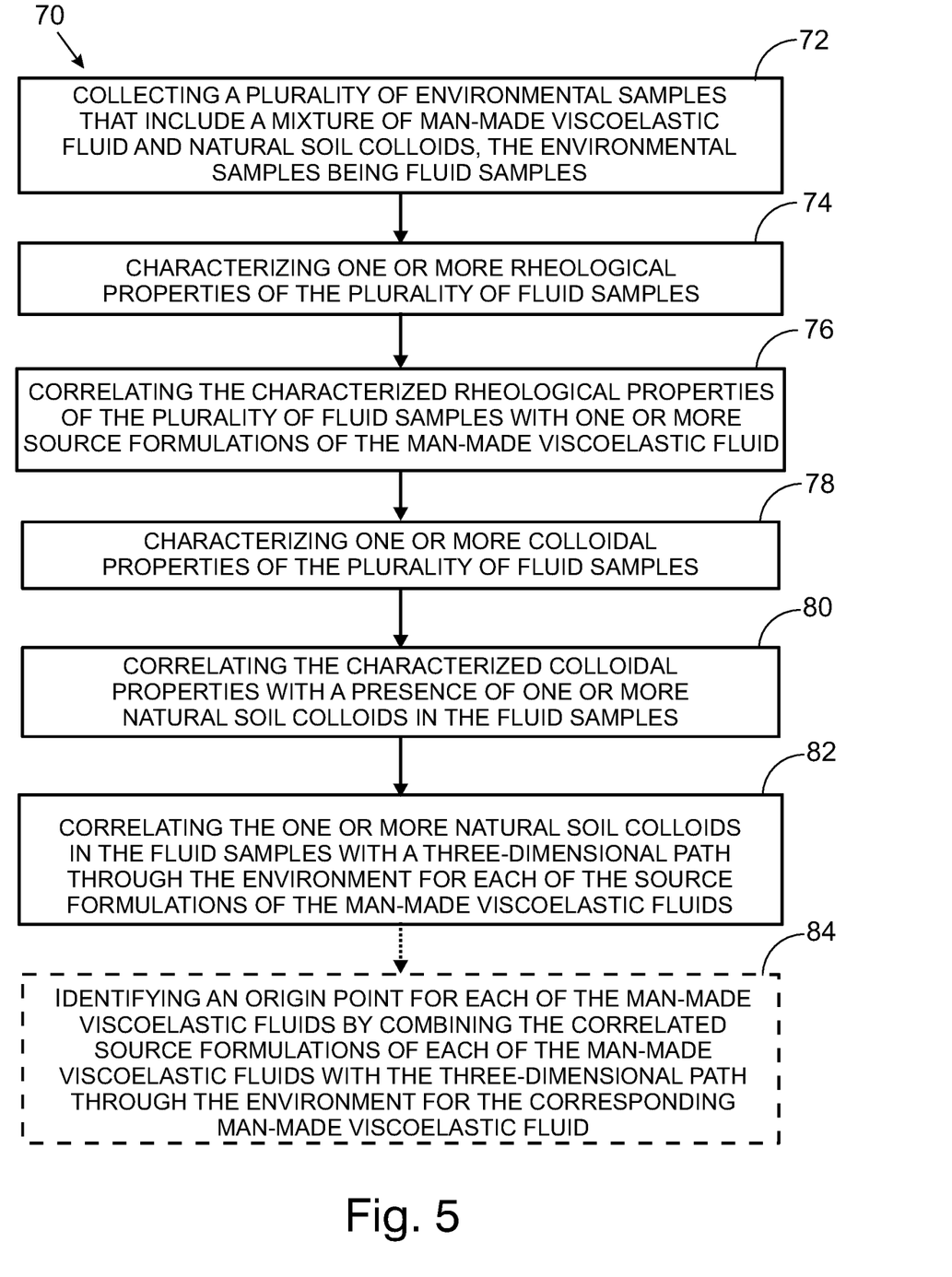
FIG. 5 is a flowchart of yet another illustrative method according to the present disclosure.

The analytical methods and strategies of the present disclosure additionally lend themselves to an advantageous method of deconvoluting an environmental contamination, as set out in flowchart 70 of FIG. 5, the method including collecting a plurality of environmental samples that include a mixture of man-made viscoelastic fluid and natural soil colloids, the environmental samples being fluid samples, at step 72 of flowchart 70; characterizing one or more rheological properties of the plurality of fluid samples, at step 74 of flowchart 70; correlating the characterized rheological properties of the plurality of fluid samples with one or more source formulations of the man-made viscoelastic fluid, at step 76 of flowchart 70; characterizing one or more colloidal properties of the plurality of fluid samples, at step 78 of flowchart 70; correlating the characterized colloidal properties with a presence of one or more natural soil colloids in the fluid samples, at step 80 of flowchart 70; and correlating the one or more natural soil colloids in the fluid samples with a three-dimensional path through the environment for each of the source formulations of the man-made viscoelastic fluids, at step 82 of flowchart 70. The method of flowchart 70 optionally further includes identifying an origin point for each of the man-made viscoelastic fluids by combining the correlated source formulations of each of the man-made viscoelastic fluids with the three-dimensional path through the environment for the corresponding man-made viscoelastic fluid, at step 84 of flowchart 70.

Figure 6:
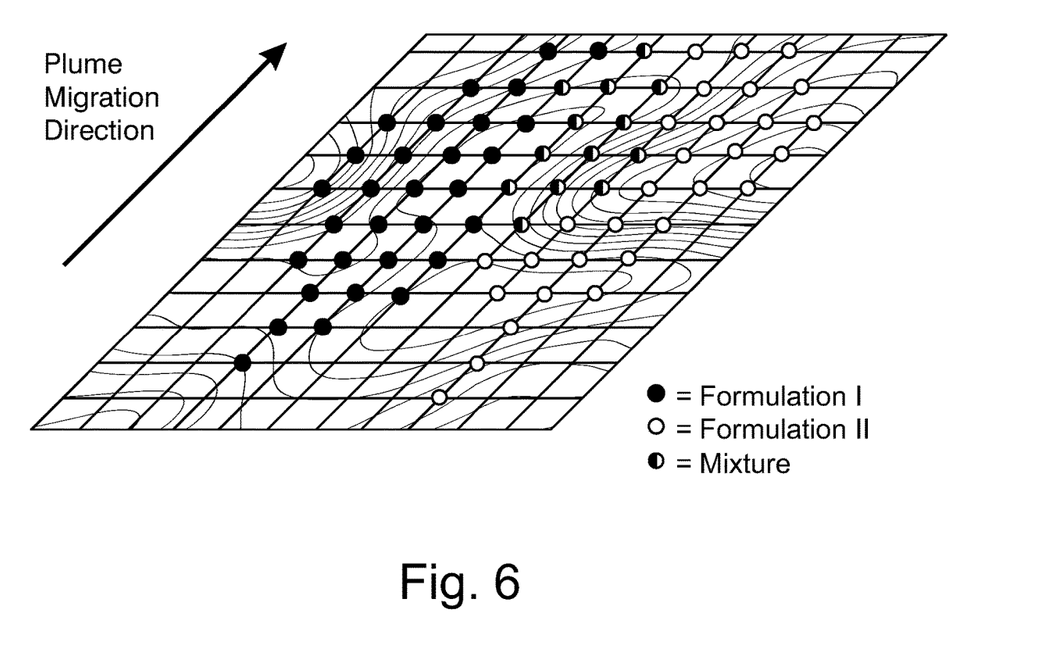
FIG. 6 is a representative illustration of contaminant mapping and deconvolution using the methods of the present disclosure.

Even where a PFAS plume may have multiple origins, if the presence, the source formulation, and the migration path through the environment for the resulting non-Newtonian LNAPLs are all determined, it may facilitate the deconvolution of the various contributors to the underground plume. For example, as shown in FIG. 6 in a simplified two-dimensional plot, the presence of two different formulations of sampled viscoelastic fluids, and their mixture, have been plotted, along with an indication of the direction of movement of each formulation, such as may be obtained by soil colloid identification. As shown, such a plot may make identification of the origin point of each formulation straightforward.

CONCLUSION

As used herein and in the claims, "substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" may be used to distinguish or identify various members of a group, or the like, and are not intended to show serial or numerical limitation.

Unless they relate to specific examples, all specifications regarding quantities and portions, particularly those for delimiting the invention, indicate a ±10% tolerance, for example: 11% means: from 9.9% to 12.1%. For terms such as "a solvent", the word "a" is not to be regarded as a numerical word but as an indefinite article or as a pronoun, unless the context indicates otherwise.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

Inventions embodied in various combinations and subcombinations of features, functions, elements, and/or properties may be claimed through presentation of new claims in a related application. Such new claims, whether they are directed to a different invention or directed to the same invention, whether different, broader, narrower or equal in scope to the original claims, are also regarded as included within the subject matter of the inventions of the present disclosure.

What is claimed is:

1. A method of detecting an environmental viscoelastic non-Newtonian light non-aqueous phase liquid (LNAPL), comprising:
    collecting an environmental sample, wherein the environmental sample is either collected as a fluid sample, or is collected as a solid that is subsequently extracted with water to generate the fluid sample; and the environmental sample is associated with a location where it was collected;
    analyzing the fluid sample using one or more rheological methods to determine one or more rheological characteristics of the fluid sample; and
    correlating the rheological characteristics of the fluid sample with a presence or an absence of the viscoelastic non-Newtonian LNAPL at the location where the environmental sample was collected.

2. The method of claim 1, wherein analyzing the fluid sample using one or more rheological methods includes characterizing one or more of
    a surface tension of the fluid sample;
    a dynamic surface energy of the fluid sample;
    an electrical conductivity of the fluid sample;
    a foaming property of the fluid sample; and
    a colloidal property of the fluid sample.

3. The method of claim 2, wherein characterizing the dynamic surface energy of the fluid sample includes:
    determining an initial surface energy of a sample substrate;
    exposing the sample substrate to the fluid sample;
    determining a post-exposure surface energy of a surface of the sample substrate;
    determining a change in surface energy of the sample substrate by comparing the initial surface energy to the post-exposure surface energy.

4. The method of claim 3, wherein characterizing the dynamic surface energy of the fluid sample further includes determining a post-exposure wetting envelope of the surface of the sample substrate.

5. The method of claim 2, wherein characterizing the colloidal property of the fluid sample includes characterizing a mixture of man-made viscoelastic fluid and a natural soil colloid in the fluid sample, and correlating the natural soil colloid in the fluid sample with a path of an environmental LNAPL as it migrated through the environment to the location where the environmental sample was collected.

6. The method of claim 1, further comprising collecting and analyzing a plurality of environmental samples, and correlating the rheological characteristics of the corresponding fluid samples with a presence or absence of a non-Newtonian LNAPL at each of the locations associated with collection of the plurality of environmental samples.

7. The method of claim 1, further comprising characterizing the environmental viscoelastic non-Newtonian LNAPL at the location where the environmental sample was collected.

8. The method of claim 7, wherein characterizing the environmental non-Newtonian LNAPL further comprises identifying one or more sources of the environmental non-Newtonian LNAPL.

9. The method of claim 1, wherein detecting the environmental non-Newtonian LNAPL includes detecting a non-Newtonian LNAPL that includes a mixture of a man-made viscoelastic fluid and a naturally-occurring soil colloid.

10. A method of identifying a source formulation for an environmental viscoelastic non-Newtonian light non-aqueous phase liquid (LNAPL), comprising:
    collecting an environmental sample, wherein the environmental sample is either collected as a fluid sample, or is collected as a solid that is subsequently extracted with water to generate the fluid sample;
    characterizing the fluid sample using one or more rheological methods to determine one or more rheological characteristics of the fluid sample; and
    correlating the determined rheological characteristics with the source formulation for the non-Newtonian LNAPL.

11. The method of claim 10, wherein the fluid sample includes a mixture of a man-made viscoelastic fluid and a naturally-occurring soil colloid, and characterizing the fluid sample using one or more rheological methods includes characterizing the colloidal properties of the fluid sample to characterize the naturally-occurring soil colloid in the fluid sample; further comprising
    correlating the naturally-occurring soil colloid in the fluid sample with a three-dimensional path of the non-Newtonian LNAPL through the environment.

12. The method of claim 11, further comprising using the identified source formulation of the non-Newtonian LNAPL and the three-dimensional path of the non-Newtonian LNAPL through the environment to identify a source for the non-Newtonian LNAPL.

13. The method of claim 10, wherein a plurality of fluid samples is collected and characterized, further comprising:
    correlating the rheological characteristics of the plurality of fluid samples with the source formulations of the non-Newtonian LNAPLs at each of the plurality of locations where the plurality of fluid samples was collected;
    analyzing colloidal properties of the plurality of fluid samples to detect and characterize natural soil colloids in the fluid sample;
    correlating the natural soil colloids in the fluid samples with three-dimensional paths of the non-Newtonian LNAPLs through the environment; and
    creating a three-dimensional map of the source formulations of the non-Newtonian LNAPLs and their paths through the environment.

14. A method of deconvoluting an environmental contamination, comprising:
    collecting a plurality of environmental samples that include a mixture of man-made viscoelastic fluid and natural soil colloids, wherein each environmental sample is either collected as a fluid sample, or is collected as a solid that is subsequently extracted with water to generate the fluid sample;
    characterizing one or more rheological properties of the plurality of fluid samples;
    correlating the characterized rheological properties of the plurality of fluid samples with one or more source formulations of the man-made viscoelastic fluid;
    characterizing one or more colloidal properties of the plurality of fluid samples;
    correlating the characterized colloidal properties with a presence of one or more natural soil colloids in the fluid samples; and
    correlating the one or more natural soil colloids in the fluid samples with a three-dimensional path through the environment for each of the source formulations of the man-made viscoelastic fluids.

15. The method of claim 14, further comprising identifying an origin point for each of the man-made viscoelastic fluids by combining the correlated source formulations of each of the man-made viscoelastic fluids with the three-dimensional path through the environment for the corresponding man-made viscoelastic fluid.

16. The method of claim 14, further comprising
    measuring one or more in situ soil parameters selected from soil moisture, soil cation exchange capacity, an elevation of a top of a capillary fringe, and a subsurface electrical conductivity and/or resistivity; and
    correlating the measured in situ soil parameters with the three-dimensional path through the environment for each of the source formulations of the man-made viscoelastic fluids.

* * * * *